United States Patent [19]

Synek

[11] Patent Number: 4,891,385
[45] Date of Patent: Jan. 2, 1990

[54] INSECTICIDAL COMPOSITIONS

[75] Inventor: Joseph Synek, Overland Park, Kans.

[73] Assignee: Mobay Corporation, Pittsburgh, Pa.

[21] Appl. No.: 324,169

[22] Filed: Nov. 23, 1981

[51] Int. Cl.$^4$ ............................................. A01N 47/10
[52] U.S. Cl. ..................................... 514/490; 514/975
[58] Field of Search ........................... 424/300; 514/490

[56] References Cited

U.S. PATENT DOCUMENTS

| | | | |
|---|---|---|---|
| 3,111,539 | 11/1963 | Böcker et al. | 560/132 |
| 3,399,991 | 9/1968 | Littler | 71/120 |
| 3,737,581 | 6/1973 | Horigome | 179/15 BT |
| 3,894,149 | 7/1975 | Mast | 424/300 |
| 3,920,441 | 11/1975 | Fischer | 71/91 |
| 4,285,968 | 8/1981 | Rose | 424/300 |
| 4,348,385 | 9/1982 | Synek | 424/300 |
| 4,388,297 | 6/1983 | Naffriger | 434/79 |

Primary Examiner—Douglas W. Robinson
Attorney, Agent, or Firm—Joseph C. Gil; Lyndanne M. Whalen

[57] ABSTRACT

Sprayable aqueous insecticidal solutions are disclosed based on a mixture of fatty acid amide emulsifiers which have been acidified to a pH of less than about 7 with a water soluble acid and thickening agents which are preferably cellulose based together with an active known insecticidal ingredient propoxur, the solutions having a final pH in the range of about 3.5 to 7.

9 Claims, No Drawings

INSECTICIDAL COMPOSITIONS

FIELD OF THE INVENTION

The present invention is concerned with ready to use sprayable aqueous insecticidal formulations.

BACKGROUND OF THE INVENTION

It has been the customary practice in the art to formulate biologically active compounds with inert diluents to facilitate the application of such compounds to their end uses. In some cases, the final formulation is undertaken by the applicator or end user while in other cases the final formulation is an item of commerce. An example of the former situation is wettable powder. The active ingredient (biologically active compound) is preliminarily compounded with diluents and agents which promote its dispersibility in water. The end user then disperses this powder into water to form a suspension having some short term stability. It is unnecessary that such formulations when diluted with water have long term storage stability. All that is required or desired is that the suspension formed by the end user have sufficient stability to permit him to prepare it and apply it. There is no need that such a suspension have stability to freeze thaw cycles. Indeed, recent developments in this field, as reflected in U.S. Pat. Nos. 3,737,581 and 3,920,441, have been to increase the concentration of active ingredients in such formulations.

Propoxur has been promoted as a 70% wettable powder and a 13% liquid solution mixed in organic solvents. In both cases, the end user must combine the purchased product with water to form a suspension with limited chemical stability. The end user must use all of the diluted product within a few days or destroy the unused portion, a serious cost effect to the user. Propoxur has been also marketed and is still being marketed as a 1% solution in kerosene in pressurized spray containers for direct utilization by the end user, since most home owners prefer not to mix the pesticide and prefer a ready-to-use material.

For a long time, there has been an interest in developing a "ready-to-use" insecticidal formulation in which the solvent was water. Such a formulation would provide a means for the ever increasing cost of petroleum products as well as the decreasing availability of them and reduce and/or eliminate the flammability problems connected with the use of these pressurized sprays. It would facilitate the use of less expensive finger sprayers, such as commonly employed for window spray and permit a greater availability of the product to those users of lower economic means as well. The commodity plastics typically used in constructing such sprayers are subject to attack and deterioration by the petroleum products traditionally used in such formulations. The use of a water based solution of the said invention would now permit such use.

The difficulties in developing such water based final formulatons have been manifold. The solution must be sufficiently stable to give the product a reasonable shelf life; in the commercial world this would be at least two to five years. Cold stability must be displayed over the wide range of temperatures encountered by products being moved in commerce without the need for special handling such as heated transport or storage facilities. Furthermore, the active ingredient itself must display chemical stability over this same period of time. The Propoxur insecticide of the present application, for instance, is subject to hydrolysis in water, particularly if the system is slightly alkaline. In addition, the viscosity of the final formulation must be sufficiently fluid to allow ready application and be sprayable, particularly from finger pump sprayers. Such sprayable formulations should not form a stable foam on being sprayed. Finally, the formulation should have a reasonable concentration of active ingredient so as to maintain an acceptable ratio of packaging cost to amount of active ingredient and so as not to require that an inordinate amount of formulation be applied to obtain effective insect control.

A water based formulation utilizing approximately 0.5 wt. % of Chlorpyrifos (Dursban or Phosphorothioic acid O,O-diethyl O-(3,5,6-dichloro-2-pyridinyl)ester) as the active ingredient has been introduced to the market in a pressurized spray can. This material is an emulsion, a disperson of a dissolved pesticide in a petroleum solvent, being dispersed in water with the aid of an emulsifier. It is not a true solution and must be shaken to be reconstituted. It must also be protected against freezing temperatures.

The propoxur active ingredient of the present application has been disclosed in U.S. Pat. No. 4,285,968 in a water based formulation but the concentration of active ingredient was kept below 0.2 wt. %, because of solubility considerations, as the practical upper limit.

SUMMARY OF THE INVENTION

The present invention comprises a clear aqueous sprayable solution of propoxur insecticide which has long term stability under field conditions including freeze thaw cycles. It has a sufficient buffering system to assure its chemical stability. It also has an overall pH of between about 3.5 and 7. A particularly suitable formulation is based per hundred parts of solution on the following:

(a) between about 8 and 12 parts of an emulsifying agent which itself comprises:
  (i) at least 50 wt. % of fatty acid amides acidified to a pH of less than 7 with a water soluble acid; and
  (ii) up to 50 wt. % of an alkyl substituted phenol ethoxylated with between 6 and 10 mols of ethylene oxide;
(b) between about 0.4 and 0.8 part of propoxur; and
(c) sufficient non-ionic thickening agent, (preferably cellulose based), to render the solution stable, most preferably between about 0.15 and 0.25 parts of a non-ionic cellulose based thickening agent having a 20° C. viscosity as a 2 wt. % solution in water of between about 10,000 and 20,000 centipoises.

DETAILED DESCRIPTION OF THE INVENTION

The propoxur of the invention is a well known insecticide, the manufacture and use of which is described in U.S. Pat. No. 3,111,539. Propoxur and aprocarb are recognized common names for 2-(2-methylethoxy)phenyl methyl carbamate which has the structural formula:

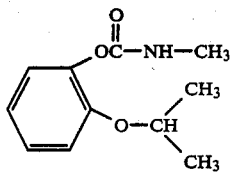

Propoxur is only slightly soluble in water, about 2000 ppm at 25° C. Furthermore, its solubility in water is less than 1000 ppm at 0° C.

The essential agent of the invention is a fatty acid amide, i.e., the reaction product of a fatty acid or mixture of acids and a mono- or difunctional amine. It is preferred to react a mixture of fatty acids or their glycerides with mono- or diethanol amine. Examples of fatty acid amides are: lauric acid diethanolamide; myristic acid diethanolamide; palmitic acid diethanolamide; oleic acid diethanolamide; stearic acid diethamolamide; isostearic acid diethanolamide; palmitoleic acid diethanolamide; linoleic acid diethanolamide; linolenic acid diethanolamide; and eleostearic acid diethanolamide. The most preferred are the diethanol amides of fatty acids having about 12-16 carbon atoms. The diethanol amide of coconut oil fatty acids is very effective.

The fatty acid amide must be acidified to a pH below 7, preferably 3.5-7, with a water soluble acid such as phosphoric acid, $(H_3PO_4)$ which is strongly preferred. Other acids such as acetic, citric and the like may be acceptable if they are compatible with the fatty acid amide.

One may use up to about 50 wt. % of other agents known as emulsifiers along with the fatty acid amide; for example, ethoxylated alkyl phenols:

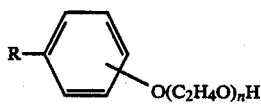

where R is $C_1$ to $C_{10}$ such as methyl, ethyl, propyl, octyl, nonyl or the like and
n is 6-12, preferably about 8.

These non-ionic emulsifiers are commercially available. A preferred compound is

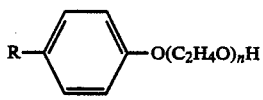

where R is octyl or nonyl and n is an average of 8-9.

The preferred thickening agent has a 10,000 to 20,000 centipose viscosity when measuring a 2% by wt. solution in water. It is preferably cellulose based but it is believed other water-soluble macro-molecular thickening agents could be used provided they meet the viscosity requirements. The amount of thickening agent required to provide such viscosity most likely will vary from compound to compound. The amount required is immaterial as long as the viscosity parameters are approached. Examples of thickening agents are cellulose substances such as: hyrocypropyl methyl cellulose, hydroxybutyl methyl cellulose, methylcellulose, oxethylcellulose, methyloxethylcellulose, ethyloxethylcellulose, carboxymethylcellulose, carboxyethylcellulose, methylcarboxymethylcellulose, ethylcarboxymethylcellulose, oxyethylcarboxymethylcellulose, sulfomethylcellulose, etc.; starch substances such as swelling starch, dextrin, methyl starch, carboxymethyl starch, etc.; plant extracts such as pectin, carragheen, tragacanth, carob bean flour, guarana flour, kelp, xanthane gum derivatives, kelzan, etc.; and synthetic substances such as polyvinyl alcohol and its water soluble derivatives.

The preparation of the stable, substantially clear sprayable aqueous solution of the invention can be done by mixing all of the components simultaneously. However, this requires high shear mixing and is not preferred because is is not necessary to go to this expense. Without being bound to the following theory, it is believed that the essential feature of the invention is that the agents, emulsifiers, and thickening agents of the type proposed, act to protect and surround the active-molecule to keep it from being exposed to conditions which could cause it to crystallize or even decompose, and permit the increase of the concentration at 0° C. from 0% propoxur to as much as 0.8% while yielding a clear stable solution. Thus, for economy, it is preferred to pre-mix the propoxur with the fatty acid amide (and optionally additional emulsifier) and add the resulting mixture to water containing the thickening agent. It is also often helpful to include some emulsifier in the water as this facilitates the preparation of the final aqueous solution.

In commercial practice, it is expected to prepare a concentrate of propoxur, diethaol amide of coconut oil fatty acid acidified to a pH of 3.5-7, and ethoxylated octyl phenol emulsifiers and then add it to a water solution of a hydroxy propyl methyl cellulose ether, isopropyl alcohol and water. Isopropyl alcohol is useful to speed up the solution of the methyl cellulose ether in the water. It is further helpful to first mix the methyl cellulose ether with isopropyl alcohol, subsequently add a small amount of emulsifier (1-5% by weight of the total employed) and then stir with an aliquot (2-5% of the total employed) of hot water (90°-100° C.) before adding to the bulk of the water at room temperature. The procedure for dispersing methyl cellulose products and the like in water is well known in the state of the art.

The principles of the invention make it feasible to prepare sprayable stable aqueous solutions of propoxur at increased concentrations up to 0.8% by weight from the known maximum of 0.2% at 25° C., but also stabilized the solution from chemical deterioration and prevents crystallization from occurring at 0° C. and below. The solubility of propoxur at 0° C. is 0% whereas the invention may contain up to 0.8% at 0° C. without crystallization occurring. Solutions with more than 0.8% by weight can be prepared but become sensitive to crystallization when temperatures drop below 5° C. In areas in the world where temperatures do not go below 5° C. it may be feasible to make a formulation of greater concentration. This increase of propoxur adds additional costs and does not increase the biological efficacy of the formula. Thus, solutions of between 0.4 and 0.8% by weight propoxur are stable over a very wide range of conditions and can be shipped throughout the world with disregard for temperatures during shipping.

It may be thought that the propoxur is being solubilized in the emulsifiers added to the formulation. This is not so and to show this we had completed the following test. Since it is important to show the effect at 0° C., the work was carried out at this temperature. The relationship of propoxur to the emulsifier is 1:9 or a 10% solution. Samples were made as follows: The propoxur was stirred in the emulsifier at 60° C. for 1 hour or more until it was dissolved.

| Example No. 1 | |
|---|---|
| Propoxur Tech | 13.0 gm. |
| Triton X100 | 87.0 gm. |
| | 100.0 gm. |
| Example No. 2 | |
| Propoxur Tech | 5.0 gm. |
| Triton X100 | 95.0 gm. |
| | 100.0 gm. |
| Example No. 3 | |
| Propoxur Tech | 1.0 gm. |
| Triton X100 | 99.0 gm. |
| | 100.0 gm. |

These samples were placed at 0° C. (32° F.) and −7° C. (20° F.) and stored until crystallization would occur and until crystallization came to an equilibrium. The samples were then checked for the amount of propoxur left in the solution above the crystals.

Examples 1 through 3 all crystallized within one day but were left for 30 days before evaluation was made. This test was repeated with the preferred fatty acid amide emulsifier and identical results were obtained. The solubility of propoxur at these temperatures, 20° F. and 32° F., in the emulsifiers was 0%.

The solubility of propoxur in isopropyl alcohol may be considered to aid in the solubilization of the propoxur. The amount soluble at 0° C. is less than 10% and at −7° C. is less than 3%. It is possible that this may aid in the increased solubility of propoxur in the formula but the use of isopropyl alcohol is to aid in the dispersion in the thickening agent. However, even at its maximum solubility the amount of isopropyl alcohol in the formula is limited to 2% or less. This amount would not increase the solubility sufficiently to increase the propoxur in water at 0° C. from 0% to 0.8%.

It is believed that we have discovered a unique and unexpected formula where propoxur can be made into a sprayable aqueous solution by the careful selection of thickening agents and emulsifiers which surround the active molecule and not only protect it from crystallization and chemical decomposition but yields a clear solution and not an opaque suspension of particles as expected.

To further prove the biological activity has not been altered a number of tests were completed showing that the formula is biologically active and the propoxur is available as an insecticide. Results of these tests will be found in the latter part of this discussion.

The invention is further illustrated, but is not intended to be limited by the following examples in which all parts and percentages are by weight unless otherwise specified.

EXAMPLES

Example 1

A concentrate and a water solution were prepared as follows:

A. A concentrate is made of about 6.25 parts of propoxur technical [98% -(1-methyl-ethoxy)phenyl methyl carbamate], about 52.08 parts of the diethanol amide of coconut oil fatty acids, acidified to a pH of about 6 with phosphoric acid, $H_3PO_4$, and about 41.67 parts of octyl phenol ethoxylated with about 9 mols of ethylene oxide (sold under the tradename Triton X-100 as one tradename of many).

B. A separate water solution is made by first combining about 0.2 parts of hydroxypropyl methyl cellulose either having a viscosity of about 15,000 centipoises as a 2 wt. % solution water at 20° C., with about 2.5 parts of isopropyl alcohol and then adding about 1 part of Triton X-100 as defined above and adding first about 2.5 parts of boiling water and then combining with about 93.8 parts of room temperature water.

C. Then about 9.6 parts of the propoxur concentrate of A are mixed with about 90.4 parts of the water solution of B to prepare about 100 parts of aqueous solution containing about 0.5% by weight of propoxur.

Portions of the aqueous solution of C were tested for cold stability and showed that the formula could be frozen solid at minus 25° C. and then allowed to thaw to a clear solution without crystallization. The formula had gone through 12 such freeze-thaw cycles with no crystallization occurring.

Accelerated storage tests as well as warehouse tests were conducted on samples prepared according to the procedure of this example but with slightly varying amounts of propoxur. The samples were stored in glass containers and at the end of two years storage under warehouse conditions of Kansas City, Mo. there was no significant loss of propoxur. Accelerated storage at 40° C. showed no significant loss of propoxur; indicating a projected shelf life for the solution of three years or more.

Example 2

The aqueous solution of Example 1C was evaluated and compared to Dursban 0.5% aqueous aerosol sold under the tradename Raid "Crack and Crevice Spray" for German Roach control and to present 13% by weight liquid concentrate of propoxur which was diluted with water to form a 0.5% emulsion (hereinafter propoxur LC). Application was mde to four different surfaces in identical concentrations with a finger pump sprayer similar to a window cleaner bottle from Example 1C and propoxur LC and with the commercial pressurized can for Dursban. Initial and residual activity were obtained as reflected in the following tables:

TABLE I

PERCENT GERMAN ROACH CONTROL AT 0 WEEK

| Treatment | Treated Surface | Percent Control After 1 hr. | 2 hr. | 4 hr. | 24 hr. |
|---|---|---|---|---|---|
| Raid (Crack/Crevice) Dursban 0.5% active ingredient | Glass | 10% | 27% | 83% | 100% |
| | Tile | 0 | 0 | 10 | 87 |
| | Painted Plywood | 3 | 3 | 30 | 87 |
| | Unpainted Plywood | 0 | 10 | 47 | 98 |
| Example 1C 0.5% active ingredient | Glass | 93 | 100 | 100 | 100 |
| | Tile | 70 | 100 | 100 | 100 |
| | Painted Plywood | 30 | 100 | 100 | 100 |
| | Unpainted Plywood | 0 | 0 | 0 | 0 |
| Propoxur LC 0.5% active ingredient | Glass | 60 | 98 | 100 | 100 |
| | Tile | 98 | 98 | 98 | 98 |
| | Painted Plywood | 13 | 57 | 60 | 73 |
| | Unpainted Plywood | 0 | 0 | 0 | 0 |
| Untreated Control | | 0 | 0 | 0 | 0 |

TABLE II

PERCENT GERMAN ROACH CONTROL AT 1 WEEK

| Treatment | Treated Surface | Percent Control After | | | |
|---|---|---|---|---|---|
| | | 1 hr. | 2 hr. | 4 hr. | 24 hr. |
| Raid (Crack/Crevice) | Glass | 0 | 0 | 23 | 100 |
| Dursban 0.5% active ingredient | Tile | 0 | 0 | 0 | 13* |
| | Painted Plywood | 0 | 0 | 0 | 57 |
| | Unpainted Plywood | 0 | 0 | 13 | 100 |
| Example 1C 0.5% active ingredient | Glass | 87 | 98 | 100 | 100 |
| | Tile | 3 | 10 | 13 | 20* |
| | Painted Plywood | 0 | 3 | 3 | 17* |
| | Unpainted Plywood | 0 | 0 | 0 | 3* |
| Propoxur LC 0.5% active ingredient | Glass | 3 | 10 | 27 | 60 |
| | Tile | 0 | 0 | 0 | 7* |
| | Painted Plywood | 0 | 7 | 7 | 23* |
| | Unpainted Plywood | 0 | 0 | 0 | 0* |
| Untreated Controls | | 0 | 0 | 0 | 0 |

TABLE III

PERCENT GERMAN ROACH CONTROL AT 2 WEEKS

| Treatment | Treated Surface | Percent Control After | | | |
|---|---|---|---|---|---|
| | | 1 hr. | 2 hr. | 4 hr. | 24 hr. |
| Raid (Crack/Crevice) | Glass | 0 | 0 | 7 | 93 |
| Dursban 0.5% active ingredient | Tile | 0 | 0 | 0 | 67 |
| | Painted Plywood | 0 | 0 | 0 | 33 |
| | Unpainted Plywood | 0 | 0 | 13 | 93 |
| Example 1C 0.5% active ingredient | Glass | 90 | 93 | 93 | 93 |
| | Tile | 93 | 93 | 93 | 100 |
| | Painted Plywood | 50 | 63 | 63 | 93 |
| | Unpainted Plywood | 0 | 0 | 0 | 3 |
| Propoxur LC 0.5% active ingredient | Glass | 13 | 20 | 38 | 70 |
| | Tile | 0 | 3 | 7 | 38 |
| | Painted Plywood | 0 | 0 | 7 | 80 |
| | Unpainted Plywood | 0 | 0 | 0 | 0 |

The aqueous solution of Example 1C indicated roach control equal to Dursban 0.5% aerosol and to standard propoxur liquid concentrate as diluted with water. However, the surfaces treated appeared to have had a significant effect on efficacy of the materials. Treatments made to low porosity surfaces (glass, tile, painted wood) indicated the solution of Example 1C to be equal to or slightly greater than Dursban 0.5% and our standard liquid formula as diluted with water. Identical treatments made to highly porous surfaces (unpainted woods) indicated detrimental effects to Example 1C and the standard liquid formula. On these surfaces (unpainted woods) Dursban 0.5% appears to be superior to Example 1C and the standard. Example 1C's speed of activity was similar to the standard formula and superior to Dursban. Roach control resulting from it generally gave effective 'knock-down' in 1-2 hours equal to the standard formula; while Dursban 0.5% required up to 24 hours for comparable activity.

A second application made after one week indicated the positive aspects of repeated applications to certain surfaces at intervals of 7 days or less.

The results from application to very porous surfaces was expected.

Example 3

Example 1 was repeated using only the diethanol amide of coconut oil fatty acids in the place of the Triton X-100. In other words a total of 53.75 parts of the diethanol amide of coconut oil fatty acids, acidified to a pH of about 6 with phosphoric acid was used in Example 1A in place of the ethoxylated nonyl phenol (Triton X-100) and 1 part was used in Example 1B to replace Triton X-100. The same result was obtained without using Triton X-100. Note that Triton X-100 is less expensive so that its use is an advantage but is not essential.

What is claimed is:

1. A stable, substantially clear sprayable aqueous insecticidal solution comprising per hundred part of solution
   (a) between about 8 and 12 parts of an emulsifying agent which comprises
      (i) fatty acid amide acidified to a pH of less than about 7 with a water soluble acid; and
      (ii) up to about 50 wt. % of alkyl substituted phenols ethoxylated with between 6 and 10 mols of ethylene oxide;
   (b) between about 0.15 and 0.25 parts of a cellulose based thickening agent with a 20° C. viscosity as a 25 wt. % solution in water of between about 10 and 20 Pa.S; and
   (c) between about 0.4 and 0.8 parts of 2(1-methylethoxy)phenyl methyl carbamate,
said solution having a pH of between about 3.5 and 7.

2. The solution of claim 1 wherein said water soluble acid is $H_3PO_4$.

3. The solution of claim 1 wherein said fatty acid amide is the diethanol amide of coconut oil fatty acids.

4. The solution of claim 1 wherein said fatty acid amide is the diethanol amide of coconut oil fatty acids, said water soluble acid is $H_3PO_4$ and the pH of said fatty acid amide is in the range of 5–6.

5. The solution of claim 1 wherein said alkyl substituted phenol is octyl phenol ethoxylated with 8–9 mols of ethylene oxide.

6. The solution of claim 1 wherein said thickening agent is hydroxy propyl methyl cellulose having a viscosity between 10,000 to 20,000 cps as a 2% by wt. solution in water at 20° C.

7. The solution of claim 1 wherein said 2(1-methylethoxy) phenyl methyl carbamate is present in a concentration of 0.4 to 0.6 parts.

8. The solution of claim 1 wherein said suspension has a pH of between 5 and 6.

9. The solution of claim 1 wherein the fatty acid amide is the diethanol amide of a fatty acid having between 12 and 16 carbon atoms.

* * * * *